United States Patent [19]

England et al.

[11] Patent Number: 5,807,407
[45] Date of Patent: Sep. 15, 1998

[54] MEDICAL IMPLANT DEVICE AND METHOD FOR MAKING SAME

[75] Inventors: Garry Lee England, Winona Lake; Richard Craig Blaschke, Warsaw, both of Ind.

[73] Assignee: Biomet, Inc., Warsaw, Ind.

[21] Appl. No.: 878,163

[22] Filed: May 4, 1992

[51] Int. Cl.$^6$ ..................................................... A61F 2/28
[52] U.S. Cl. ................................................ 623/16; 623/23
[58] Field of Search ............................. 623/16, 18; 427/2

[56] References Cited

U.S. PATENT DOCUMENTS

| | | |
|---|---|---|
| 3,605,123 | 9/1971 | Hahn . |
| 4,146,936 | 4/1979 | Aoyagi et al. ............................. 623/16 |
| 4,239,827 | 12/1980 | Notaro . |
| 4,486,470 | 12/1984 | Stuck et al. .............................. 427/196 |
| 4,617,197 | 10/1986 | Rittner et al. . |
| 4,626,209 | 12/1986 | Tsai et al. . |
| 4,644,942 | 2/1987 | Sump . |
| 4,702,930 | 10/1987 | Heide et al. . |
| 4,784,159 | 11/1988 | Szilagyi . |
| 4,846,834 | 7/1989 | von Recum et al. . |
| 4,854,496 | 8/1989 | Bugle . |
| 4,871,366 | 10/1989 | Von Recum et al. ..................... 623/11 |
| 4,917,702 | 4/1990 | Scheicher et al. . |
| 5,004,476 | 4/1991 | Cook . |
| 5,012,853 | 5/1991 | Bihlmaier . |
| 5,037,928 | 8/1991 | Li et al. . |
| 5,047,054 | 9/1991 | Vijayan et al. ........................... 623/16 |
| 5,085,866 | 2/1992 | Cowsar et al. . |
| 5,122,385 | 6/1992 | Dahar et al. . |
| 5,158,804 | 10/1992 | Alkan et al. . |
| 5,169,597 | 12/1992 | Davidson et al. . |
| 5,201,766 | 4/1993 | Georgette . |
| 5,258,030 | 11/1993 | Wolfarth et al. . |
| 5,282,861 | 2/1994 | Kaplan ...................................... 623/16 |
| 5,292,596 | 3/1994 | Privett, III et al. . |
| 5,296,667 | 3/1994 | Marantz et al. . |

FOREIGN PATENT DOCUMENTS

| | | |
|---|---|---|
| 130188 | 2/1984 | Japan . |
| 2216425 | 10/1989 | United Kingdom ..................... 623/22 |
| 9006139 | 6/1990 | WIPO . |
| 9006140 | 6/1990 | WIPO . |
| 9310953 | 6/1993 | WIPO . |

OTHER PUBLICATIONS

"CP3–60: Cold Isostatic Press", ISO–Spectrum Inc. brochure (pre–Jan. 21, 1992).

"HP6–30: Hot Isotatic Press", ISO–Spectrum Inc. brochure (pre–Jan. 21, 1992).

"Automated IsoPress", *ABB Autoclave Systems, Inc.* Technical Bulletin 5319 (pre–Jan. 21, 1992).

Pending U.S. application Serial No. 08/006,740, filed Jan. 21, 1993, titled "Medical Implant Device and Method for Making Same".

Price, P., and Kolhler, S., "Hot Isostatic Pressing of Metal Powders," *Metal Handbook*, pp. 419–443, 1983.

"High Performance Ceramics, the future materials—available today," *ABB Cerama AB* brochure, May 1988.

"Hot Isostatic Pressing: Gets Bigger, Hotter and More Flexible," *Carbide & Tool*, v. 19, No. 2, May–Jun. 1987.

Price, P., and Kolhler, S., "Cold Isostatic Pressing of Metal Powders," *Metal Handbook*, pp. 444–450, 1983.

Hanes, Hugh D., "Isostatic Pressing: stating the art," *Tooling and Production—Series on basic manufacturing techniques*—No. 5.

*Primary Examiner*—David Isabella
*Attorney, Agent, or Firm*—Harness, Dickey & Pierce, P.L.C.

[57] ABSTRACT

A medical implant device being operable to replace at least a portion of the natural joint in a human. The medical implant device includes a structural member being composed of a composite material. The medical implant device further includes a metallic porous coating disposed on at least a portion of the exterior of the structural member.

13 Claims, 3 Drawing Sheets

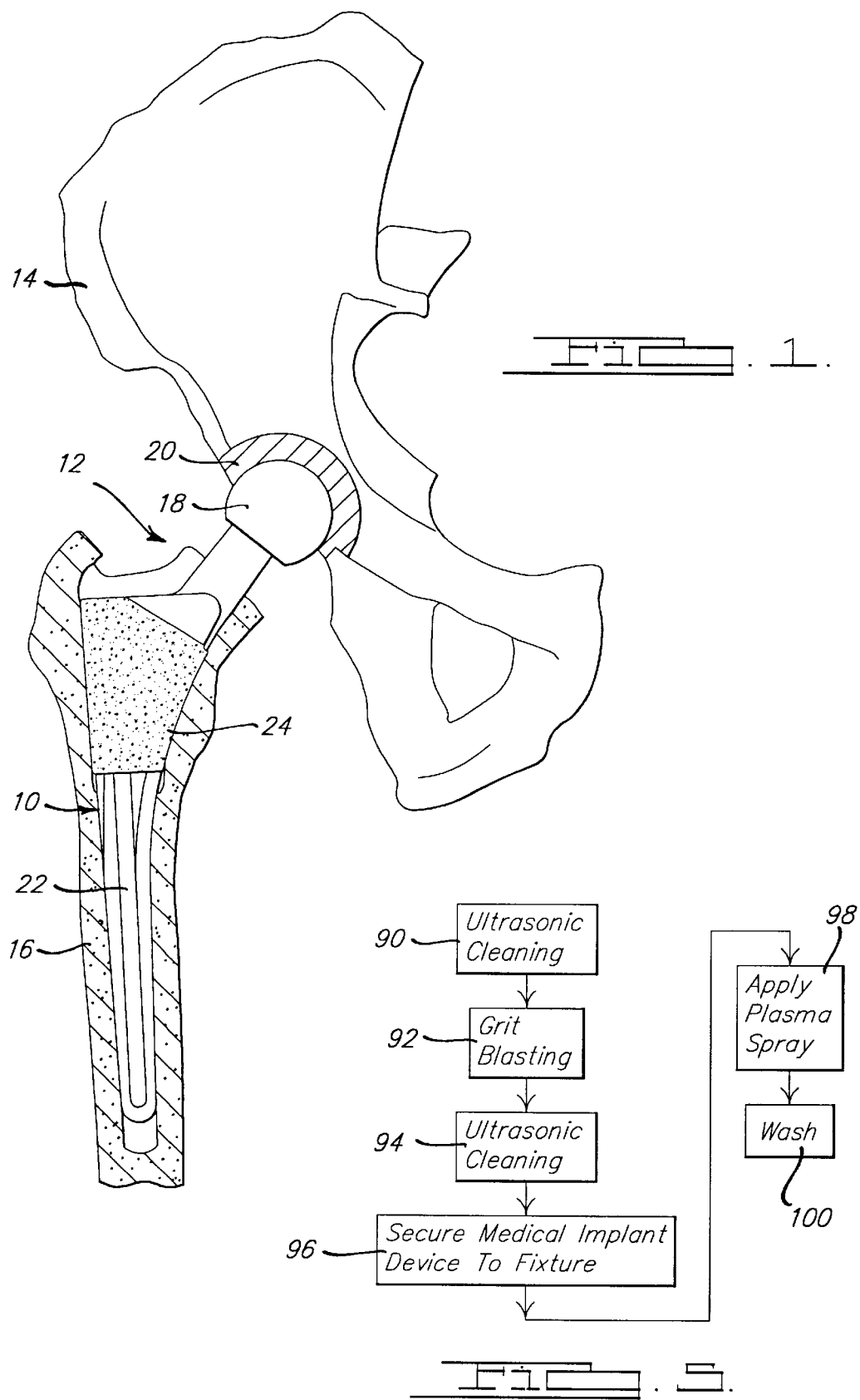

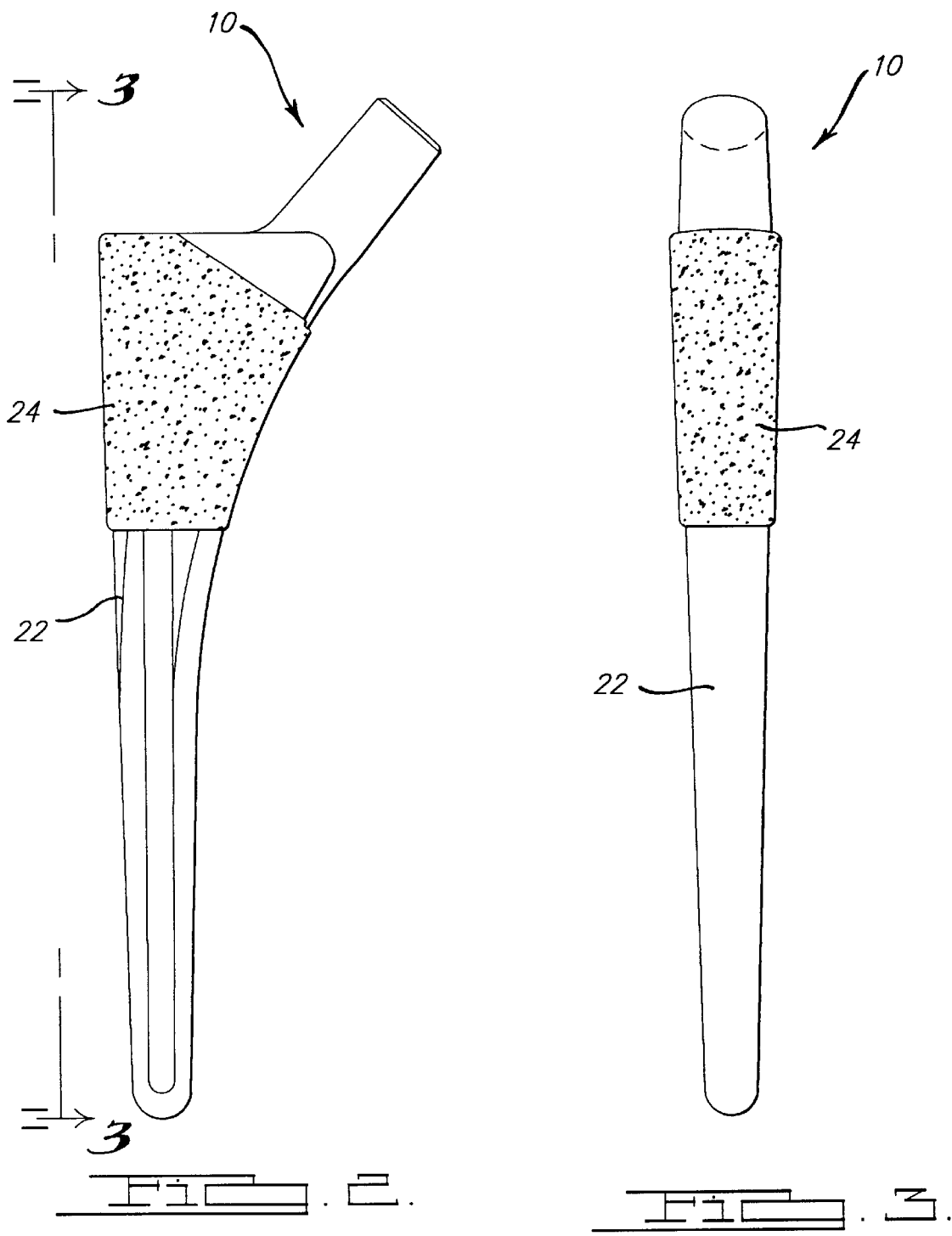

MEDICAL IMPLANT DEVICE AND METHOD FOR MAKING SAME

BACKGROUND OF THE INVENTION

This invention relates generally to medical implant devices, and more particularly to medical implant devices which are formed from a composite material.

A natural joint in the human body, such as a hip joint, may undergo degenerative changes due to a variety of etiologies. When these degenerative changes become advanced and are irreversible, it may ultimately become necessary to replace the natural joint with a prosthetic joint. Such a prosthetic joint is often formed from a high-strength material which is not only able to accommodate the various loading conditions that the artificial joint may encounter, but is also biocompatible with the human body.

When loading conditions for prosthetic joints are relatively extreme such as in the case of artificial hips, prosthetic joints may be made from metal alloys such as titanium or cobalt chrome alloys. Not only are these metal alloys of sufficient strength to withstand relatively extreme loading conditions, but due to their metallic nature, a metallic porous coating typically of Ti-6Al-4V may be secured to the metal alloy by a metallic bond. Such metallic porous coatings are useful for providing initial fixation of the implant immediately after surgery, but also serve to facilitate long-term stability by enhancing bone ingrowth/upgrowth.

While medical implant devices made from biocompatible metal alloys are effective, they may not have certain desirable characteristics which are associated with composite materials such as polysulfone. For example, composite materials are relatively flexible and therefore tend to distribute load more evenly than implants made from metal alloys. In addition, by controlling the orientation as well as the amount of carbon fibers in an implant formed from a composite material, it is possible to control the structural modulus of the implant. This characteristic may be of particular importance with certain implants such as artificial hips where it may be desirable to maintain a relatively constant structural modulus even though the size of the implant may vary to accommodate different patients.

Despite the potential advantages of composite materials described above, composite materials have not generally been used for load bearing medical implant devices because of problems associated with fixation. In particular, it is generally not possible to texture the outer surface of an implant formed from a composite material to obtain a relatively high degree of roughness or porosity which is necessary to provide adequate initial fixation and to promote bone ingrowth/upgrowth. While GB 2 216 425A describes a medical implant that has a textured pad that is secured to a substrate, the pad represents a separate physical structure that is bonded to the surface of the implant.

SUMMARY OF THE INVENTION

An advantage of the present invention is to provide a medical implant device which is made from a high-strength material which is relatively flexible.

A further advantage of the present invention is to provide a medical implant device in which the structural modulus of the material forming the implant may be controlled so as to permit the implant to more closely function in a manner which approximates the functioning of the natural joint.

Another advantage of the present invention is to provide a medical implant device which is formed from a composite material which has a rough or porous coating which is able to secure the medical implant device to bone.

The invention, in one form thereof, provides a medical implant device which is operable to replace at least a portion of a natural joint in a human. The medical implant device includes a structural member which is composed of a composite material. The medical implant device further includes a metallic coating disposed on a portion of the exterior of the structural member.

The invention further provides, in another form thereof, a method of manufacturing a medical implant device which is operable to replace at least a portion of a natural joint in a human. The method comprises several essential steps, including the initial step of forming a structure member from a composite material. According to a further step of the invention, a porous coating is then applied to at least a portion of the exterior of the structural member.

BRIEF DESCRIPTION OF THE DRAWINGS

Various advantages of the present invention will become apparent to one skilled in the art upon reading the following specification and by reference to the following drawings in which:

FIG. 1 is an elevational view of a medical implant device according to the teachings of the preferred embodiment of the present invention shown in operative association with a hip and a pelvis;

FIG. 2 is an elevational view of a medical implant device shown in FIG. 1 according to the teachings of the preferred embodiment of the present invention;

FIG. 3 is an elevational view of the medical implant device according to the teachings of the preferred embodiment of the present invention taken along the lines 3—3 in FIG. 2;

FIG. 5 is a diagrammatic representation of the process steps involved in an exemplary embodiment of the method of the present invention.

DETAILED DESCRIPTION OF THE PREFERRED EMBODIMENT

Figure 4:
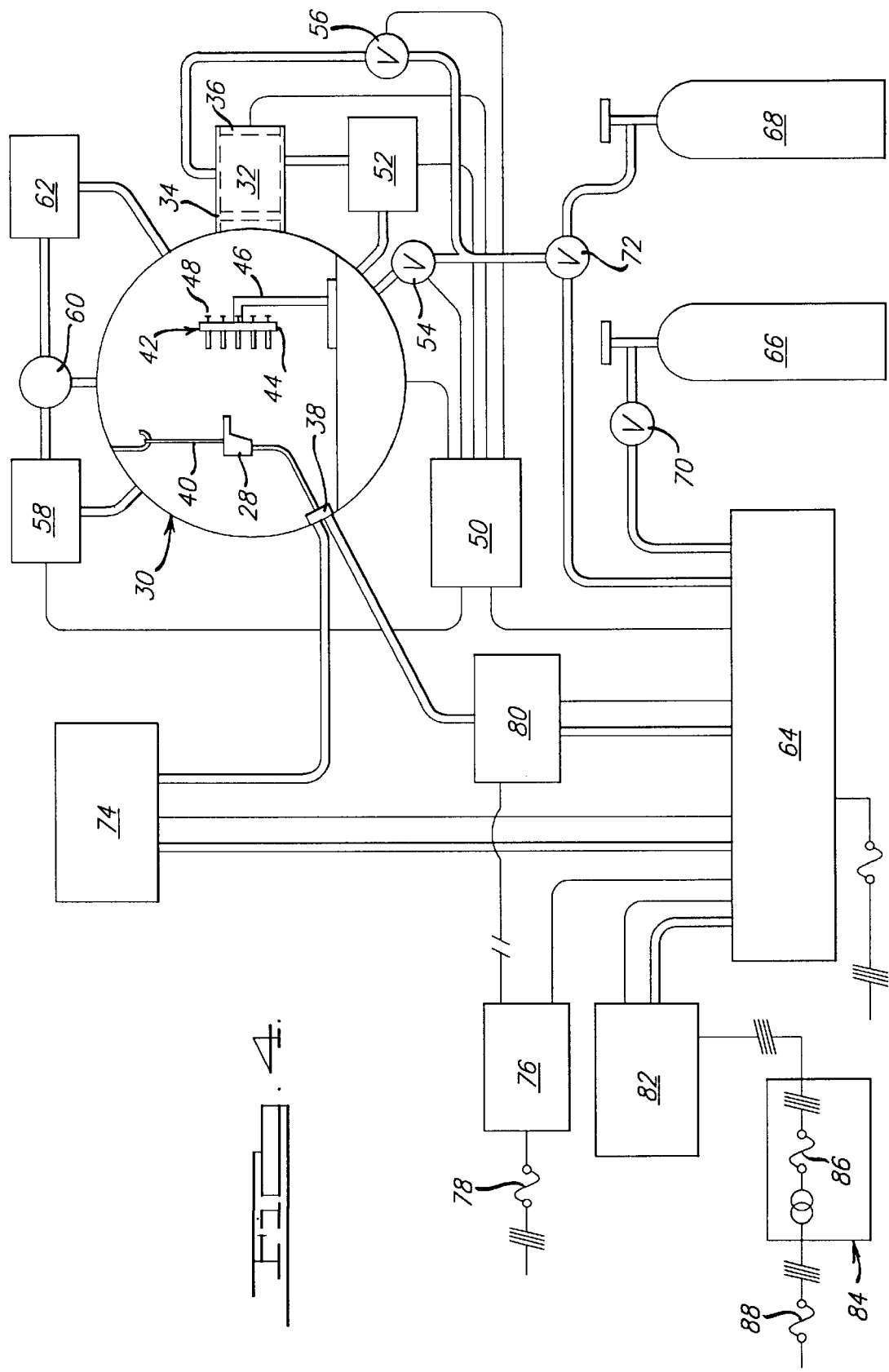
FIG. 4 is a diagrammatic illustration of the apparatus used for applying the porous coating to the medical implant device shown in FIG. 2 according to the teachings of the preferred embodiment of the present invention.

The following discussion of the preferred embodiment of the present invention is merely exemplary in nature and is in no way intended to limit the invention or its application or uses.

Referring now to FIG. 1, a medical implant device 10 is shown according to the preferred embodiment of the present invention. The medical implant device 10 is represented as a femoral hip stem of a hip joint prosthesis 12 which is used for transferring a load between the pelvis 14 and the femur 16. As will be appreciated by those skilled in the art, the hip joint prosthesis 12 further includes a head component 18 for engaging an acetabular component 20 which is secured to the pelvis 14. While the medical implant device 10 takes the form of a femoral hip stem, it will be understood that the present invention may also be equally applicable to other types of prosthetic components including an acetabular component for a hip joint prosthesis, a femoral component for a knee joint prosthesis, a tibial plateau for a knee joint prothesis as well as other types of medical implant devices.

The medical implant device includes a structural member 22 which is used for transferring loading between the pelvis 14 and the femur 16. The structural member 22 is preferably formed of a biocompatible thermoplastic having a biocompatible fibrous material disposed therein. The biocompatible thermoplastic may be polysulfone, polyether ether ketone (PEEK), or poly aryl ether ketone (PAEK), though other suitable materials may be used. The amount and orientation of the biocompatible fibrous material within the structure member 22 is selected to achieve the desired structural modulus for the medical implant device 10. The biocompatible fibrous material may be either continuous or chopped carbon fibers, though other suitable materials may be used.

To provide means for securing the structural member 22 to the femur 16, the medical implant device 10 further includes a porous coating 24. The porous coating 24 provides for initial fixation of the medical implant device 10 immediately after surgery. In addition, the porous coating 24 permits bone upgrowth/ingrowth to occur which further secures the medical implant device 10 to the femur 16. The porous coating 24 may be made from a titanium alloy such as Ti-6Al-4V, commercially pure titanium, a cobalt chrome alloy or other biocompatible metal alloys. While the porous coating 24 may be applied by a flame spray, plasma spray or sputtering techniques, it will be appreciated that other suitable methods may be used.

Because the structural member 22 of the medical implant device 10 is made from a composite material, the medical implant device 10 is relatively flexible and therefore tends to distribute load more evenly than if the structural member 22 were made from metal alloys. In addition, by controlling the orientation as well as the amount of the biocompatible fibrous material within the structural member 22, it is possible to control the structural modulus of the medical implant device 10. This permits the functional characteristics of the medical implant device to more closely approximate the characteristics of the natural component of the human body which is replaced by the medical implant device 10. In addition, the porous coating on the medical implant device 10 provides initial fixation of the device 10 immediately after surgery as well as provides long-term stability by enhancing bone ingrowth/upgrowth.

The apparatus 26 for applying the porous coating to the structural member will now be described with reference to FIG. 4. The apparatus 26 includes a plasma spray gun 28 which is disposed within a spray chamber 30. The plasma spray gun 28 receives a controlled mixture of helium and argon as well as a powdered material such as Ti-6Al-4V which is used to form the porous coating 24. The plasma spray gun 28 ionizes the mixture of helium and argon to form a plasma which has a temperature of approximately 17,000° F. by creating a relatively large voltage differential between the anode and cathode of the plasma spray gun 28. The powdered material which forms the porous coating 24 is then injected at a point just in front of the plasma leaving the plasma spray gun 28 such that melted particles of the powdered material melt a portion of the structural member 22 and become partially embedded on the outer surface of the structural member 22. The melted particles leaving the plasma spray gun 28 have a velocity of between 400 and 600 meters per second. While the plasma spray gun 28 may be Model No. F4-HB available from Plasma-Technik AG, other suitable plasma spray guns may be used.

The spray chamber 30 includes a pass-through chamber 32 having an internal door 34 and an external door 36. The external door 36 is used to allow the medical implant device 10 to be placed within the pass-through chamber 32 and then permits the pass-through chamber 32 to be sealed from the environment while the medical implant device 10 is removed through the inner door 34 and placed on a fixture described below. The spray chamber 30 further includes a plasma hook-up feed 38 which is used to deliver power, the powdered material, and gases to the plasma spray gun 28. In addition, the spray chamber 30 further includes a counterbalancing device 40 which is secured to the plasma spray gun 28 and allows the plasma spray gun 28 to be manipulated by the operator without causing the weight of the plasma spray gun 28 to fatigue the operator. While the spray chamber 30 may be that which is available from Mill Lane, Lowell, Mass., other suitable spray chambers may be used.

Disposed within the spray chamber 30 is a fixture 42 for supporting a plurality of medical implant devices 10 within the spray chamber 30. The fixture 42 includes an annular member 44 which is used to receive approximately six medical implant devices 10. The annular member 44 is able to rotate with respect to a support member 46 so as to allow the operator of the plasma spray gun to have relatively easy access to each of the medical implant devices 10. In addition, the annular member 44 includes a plurality of knobs 48 which permit rotation of each of the medical implant devices 10 individually with respect to the annular member 44 so as to allow all surfaces of each medical implant device 10 to be accessible to the operator of the plasma spray gun 28.

To control the operation of the spray chamber 30, the apparatus 26 further includes a chamber controller 50. The chamber controller 50 is used to control the evacuation of the spray chamber 30 and the pass-through chamber 32 by means of a vacuum pump 52. The vacuum pump 52 has the capacity to reduce the pressure within the spray chamber 30 as well as the pass-through chamber 32 to approximately 10 millitorr. In addition, the chamber controller 50 is able to control the pressure in the spray chamber 30 and the pass-through chamber 32 during the plasma spray operation through the valves 54 and 56. The chamber controller 50 is connected to a control unit which is more fully described below. While the chamber controller 50 may be that which is available from Vergason Technologies, Inc., Spencer, N.Y., other suitable chamber controllers may be used. While the vacuum pump 52 may be Model No. 212-H-10 which is available from Stokes Vacuum, Philadelphia, Pa., other suitable vacuum pumps may be used.

As will be appreciated by those skilled in the art, the spray chamber 30 becomes hot during the plasma spray operation. To remove heat from the spray chamber 30 during this operation, the apparatus 26 further includes a chamber blower 58, a tube cooler 60, as well as a chamber chiller 62. The chamber blower 58 is controlled by the chamber controller 50 and is used to receive heated argon and helium from the spray chamber 30 and deliver the gas to the tube cooler 60. The tube cooler 60 has a plurality of half-inch diameter copper tubes having ethylene glycol flowing therethrough which act as a heat exchanger. The chamber chiller 62 is in turn used to cool the ethylene glycol flowing in the tube cooler 60 to approximately 0° C. The argon and helium which has passed through the tube cooler 60 is then reintroduced into the spray chamber 30. The tube cooler 60 may be Model No. UU 0420 RAHM 00-5 available from Hi-Ross, while the chamber chiller 62 may be a 20 ton chiller available from AEC of Elk Grove Village, Ill. However, other suitable chillers and tube access may be used.

The apparatus further includes a control unit 64 which is used to control the flow of argon and helium as well as control the current which is delivered to the plasma spray gun 28. The control unit 64 also serves to control the speed at which the powder is delivered to the plasma spray gun 28 as more fully described below, as well as monitors the temperature at which the plasma spray gun 28 operates by recording the temperature of the water leaving the plasma spray gun 28. In addition, the control unit 64 determines whether the pressure of argon gas delivered to the plasma spray gun 28 is within a predetermined range. If either the pressure of the ionizing gases delivered to the plasma spray gun 28 falls outside the predetermined range or the temperature of the water from the plasma spray gun 28 becomes too high (e.g., exceeds 35° C.), the control unit 64 terminates the plasma spray operation until these conditions are corrected. The control unit 64 also monitors the ratio of argon to helium delivered to the spray chamber 30 during the plasma spray operation so as to maintain a ratio of 30 standard liters of argon to 10 standard liters of helium. While the control unit 64 may be Model No. PT-M1000 available from Plasma-Technik AG, other suitable control units may be used.

The control unit 64 receives helium gas from a first tank 66 through a first regulator diaphragm valve 70 as well as argon gas through the second regulator diaphragm valve 72. The second regulator diaphragm valve 72 also controls the flow of argon gas to the electronically actuated valves 54 and 56 which in turn controls the flow of argon gas to the spray chamber 30 as well as the pass-through chamber 32. While the control unit 64 may be Model No. PT-M1000 available from Plasma Technik AG, other suitable control units may be used.

To deliver powdered material which is used to form the porous coating to the plasma spray gun 28, the apparatus 26 further includes a powder feeder 74. The powder feeder 74 is controlled by the control unit 64 and is used to simultaneously deliver two grades of powdered Ti-6Al-4V to the plasma spray gun 28. The first powder is a fine grade of 80–200 mesh, while the second powder is a coarse grade of 60–100 mesh. Powders which have been specially developed and tested for Plasma-Technik AG equipment, such as Plasmatex powders, are preferable, though other suitable powders may be used. Both the fine and coarse grades of powder are delivered to the plasma spray gun 28 by a flow of argon gas which is delivered from the control unit 64. The flow rate of argon gas for the fine grade powder is 2.3 liters/minute while the flow rate for the course grade is 2.6 liters/minute. The wheel speed associated with the powder feeder 74 is 16% of the maximum wheel speed for the fine grade powder, while the wheel speed associated with the course grade powder is 15% of the maximum. However, it will be understood that the flow rate of the gas, current and powder feed rates may be those valves which are recommended for the particular type of the powder which is used. While the powder feeder 74 may be a Powder Feeder Twin 10 available from Plasma-Technik AG, other suitable powder feeders may be used.

To supply power for operating the control unit 64 as well as the plasma spray gun 28, the apparatus 26 further includes a first power supply 76. The first power supply 76 receives electrical energy from a source (not shown) through a slow burning 300 amp fuse 78. The first power supply 76 is able to generate 105 KVA and is used to supply the control unit 64 as well as the plasma spray gun 28 through a jam box 80. While the first power supply 76 may be a Model No. PT 800 available from Plasma-Technik AG, other suitable power supplies may be used.

The apparatus 26 further includes a freon chiller 82 which is used to cool the water which circulates through the plasma spray gun 28. The freon chiller 82 is controlled by the control unit 64 and delivers cooling water to the control unit 64 which in turn is delivered to the plasma spray gun 28. In this regard, the freon chiller 82 preferably cools the water entering the plasma spray gun 28 to approximately 17° C. Electrically communicating with the freon chiller 82 is a second power supply 84 which is used to provide a regulated supply of voltage to the freon chiller 82. The second power supply 84 includes a 35 amp slow burning fuse 86 and receives power from a source (not shown) through a 60 amp slow burning fuse 88. While the freon chiller may be model No. FK6695 available from Plasma-Technik AG, other suitable freon chillers may be used.

An example of the operation of the apparatus 26 will now be described with reference to FIG. 5. Prior to placing the structural member 22 in the spray chamber 30, the structural member 22 is first ultrasonically cleaned in water to remove surface contaminants as indicated by the step 90. Following the first ultrasonic cleaning step 90, the structural member 22 is subjected to a grit blasting operation as represented by the step 92. In this regard, the areas of the structural member 22 which are to be free of the porous coating is initially covered with polyvinyl chloride tape. The structural member 22 is then placed in front of the grit blaster operating at 40 psi with a half-inch nozzle and using 16 grit silicon carbide particles. By grit blasting the structural member 22, a roughened surface is formed in the region which is exposed to the particles.

The polyvinyl chloride tape is removed and the structural member 22 is then cleaned in a second ultrasonic cleaning operation as represented by the step 94. The portions of the structural member 22 which are not to be covered by the porous coating 24 are then covered by heat tape which is resistant to the high temperatures which are generated during the plasma spraying operation. Care is taken so that the portions of the structural member 22 which are to be covered by the porous coating 24 are not physically contacted after the second ultrasonic cleaning step 94 until after the porous coating 24 has been applied. In this regard, the storage racks which are used to transport the structural member 22 may support the structural member 22 only at those areas which are not to be coated with the porous coating 24.

The spray chamber 30 is initially evacuated to approximately 10 millitorr by the vacuum pump 52 and then backfilled with argon gas to a pressure slightly above atmospheric. The structural member 22 is then placed in the pass-through chamber 32 through the exterior door 36 and then the pass-through chamber 32 is closed. The operator of the spray chamber 30 then uses the gas-impermeable arm length rubber gloves within the spray chamber 30 to open the inner door 34 of the pass-through chamber 32, remove the structural member 22 and secure the structural member 22 to the fixture 42 as indicated by the step 94. Again, care is taken to make sure that no contact is made with the portions of the structural member 22 which are to receive the porous coating 24.

At step 96, the operator of the spray chamber 30 directs the plasma spray gun 28 at one of the structural members 22 on the fixture 42 while the structural member 22 is rotated by using one of the knobs 28. The plasma spray is then applied to the structural member 22 for a period of approximately 20 seconds after which the annular member 44 is rotated in such a manner as to place the structural member 22 to which the plasma spray has been applied proximate to the exhaust of the tube cooler 60 for approximately one minute. By placing the structural member 22 in front of the exhaust of the tube cooler 60 immediately after receiving the plasma spray, the thermal energy within the structural member 22 is able to dissipate a sufficient amount so as to prevent the structural member 22 from melting.

While one of the structural members 22 is in front of the exhaust of the tube cooler 60, the operator may begin the process of applying the porous coating 24 on to another structural member 22 in the same manner as described above. This process continues until each of the structural members 22 on the fixture 42 has received one application of plasma spray. Once each of the structural members 22 has received one application of plasma spray, the process is repeated until eight coatings have been applied to each of the structural members 22. After each of the structural members 22 have received eight applications of plasma spray, each of the structural members 22 with the porous coating 24 are removed from the spray chamber 30 through the pass-through chamber 32 and then each of the medical implant devices 10 are sandpapered to remove loose material and then are washed in a water jet operating at 900 psi to remove additional residue as indicated by step 100.

The foregoing discussion discloses merely exemplary embodiments of the present invention. It will be appreciated that the structural member may be coated with a thermoplastic resin prior to the application of the plasma spray. In addition, the present invention may be used in conjunction with a variety of prosthetic devices such as acetabular components, femoral and tibial components of prosthetic knee joints, as well as other types of medical implants. The porous coating may also be coated with an osteoconductive material such as hydroxyapatite, fluorapatite, or other similar materials. It will therefore be appreciated that the above discussion is presented only by way of illustration and not by way of any limitation, and that various alternatives and modifications may be made to the illustrative embodiment without departing from the spirit and scope of the invention.

What is claimed is:

1. A method for manufacturing a medical implant device which is operable to replace at least a portion of a natural joint in a human, said method comprising the steps of:

forming a structural member from a composite material, said structural member having an exterior; and applying a metallic porous coating to at least a portion of the exterior of said structural member, said step of applying a metallic porous coating includes the step of securing a thermally sprayed metal to said structural member by melting at least a portion of the exterior of said structural member.

2. The medical implant device manufactured by the method set forth in claim 1.

3. The method for manufacturing a medical implant device of claim 1, wherein said step of forming a structural member includes the step of orienting fibers in said structural member to control the structural modulus of said structural member.

4. The method for manufacturing a medical implant device of claim 1, wherein said step of forming a structural member includes the step of forming said structural member from biocompatible thermoplastic selected from the group consisting of polysulfone, polyether ether ketone, and poly aryl ether ketone.

5. The method of claim 4, wherein said step of applying a metallic porous coating comprises the step of applying to said structural member a porous layer of an alloy of a material selected from the group consisting of titanium and cobalt chrome.

6. The method for manufacturing a medical implant device of claim 1, wherein said step of applying a metallic porous coating includes the steps of repeatedly:

(a) applying a plasma spray to a said structural member, said plasma spray including a metal used in forming said metallic porous coating, and (b) removing said plasma spray from said structural member, whereby said metallic porous coating is secured to said composite material by melting portions of the exterior of said structural member.

7. The method of claim 1, further comprising the additional step of grit blasting said structural member before said metallic coating is applied.

8. A porous coated medical implant device prepared by the process of:

forming a structural member from a composite material having fibers oriented to obtain a desired structural modulus, said structural member having an exterior;

locating said medical implant device in a spray chamber; and applying a plasma spray having a metallic material to said structural member so as to secure said metallic material to said structural member.

9. The porous coated medical implant device of claim 8, wherein:

said structural member is formed from a material selected from the group consisting of polysulfone, polyether ether ketone, and poly arly ether ketone; and said metallic material is formed from an alloy of a material selected from the group consisting of titanium and cobalt chrome.

10. The porous coated medical implant device of claim 9, wherein said step of applying a plasma spray includes the steps of repeatedly:

(a) applying said plasma spray to said structural member, and (b) removing said plasma spray from said structural member, whereby said metallic material is secured to said composite material by melting a portion of the exterior of said structural member.

11. The porous coated medical implant device of claim 10, wherein said structural member includes a layer of thermoplastic resin.

12. The porous coated medical implant device of claim 11, further prepared by the additional step of grit blasting said structural member before said plasma spray is applied to said structural member.

13. The porous coated medical implant of claim 12, wherein said porous coated medical implant forms a portion of a hip joint prosthesis.

* * * * *